United States Patent
Masuda et al.

(10) Patent No.: US 7,202,283 B2
(45) Date of Patent: Apr. 10, 2007

(54) METHOD FOR DISSOLVING SATURATED POLYESTER SOLUTION FOR DECOMPOSING SATURATED POLYESTER AND METHOD FOR DECOMPOSITION USING THE SAME

(75) Inventors: Hisayo Masuda, Shimodate (JP); Katsuji Shibata, Shimotsuma (JP); Hiroyuki Izawa, Tsukuba (JP); Ayako Iwamaru, Oyama (JP)

(73) Assignee: Hitachi Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/495,592

(22) PCT Filed: Nov. 13, 2002

(86) PCT No.: PCT/JP02/11836

§ 371 (c)(1),
(2), (4) Date: Sep. 20, 2004

(87) PCT Pub. No.: WO03/042288

PCT Pub. Date: May 22, 2003

(65) Prior Publication Data

US 2005/0027023 A1 Feb. 3, 2005

(30) Foreign Application Priority Data

| Nov. 16, 2001 | (JP) | 2001-351068 |
| Nov. 16, 2001 | (JP) | 2001-351073 |
| Nov. 16, 2001 | (JP) | 2001-351076 |
| Nov. 16, 2001 | (JP) | 2001-351081 |
| Nov. 16, 2001 | (JP) | 2001-351082 |

(51) Int. Cl.
*C08J 11/04* (2006.01)
*C07C 69/76* (2006.01)

(52) U.S. Cl. .................... 521/48.5; 560/76; 560/78; 521/48

(58) Field of Classification Search ............... 521/48, 521/48.5; 560/76, 78
See application file for complete search history.

(56) References Cited

U.S. PATENT DOCUMENTS 4,055,534 A * 10/1977 Gerber ............... 524/153
4,078,916 A 3/1978 Gerber et al.

FOREIGN PATENT DOCUMENTS

| DE | 26 26 358 A1 | 12/1976 |
| JP | 08-253619 | 10/1996 |
| JP | 11-302208 | 11/1999 |
| JP | 11-322677 | 11/1999 |
| JP | 2000-053802 | 2/2000 |
| JP | 2000-169623 | 6/2000 |
| JP | 2000-191766 | 7/2000 |
| JP | 2000-198876 | 7/2000 |
| JP | 2000-218167 | 8/2000 |
| JP | 2000-302707 | 10/2000 |
| JP | 2000-327828 | 11/2000 |
| JP | 2001-192492 | 7/2001 |
| WO | WO 97/24310 | 7/1997 |

OTHER PUBLICATIONS

International Search Report for PCT/JP02/11836, mailed Mar. 4, 2003.
German Official Action w/English translation, mailed Jul. 29, 2005, for Application No. 102 97 453.5-43 (6 pp.).
Official Action for Application No. 02822659.3, issued Dec. 9, 2005.

* cited by examiner

*Primary Examiner*—Sameul A. Acquah
(74) *Attorney, Agent, or Firm*—Antonelli, Terry, Stout and Kraus, LLP.

(57) ABSTRACT

The present invention provides a dissolution method for saturated polyester capable of recycling saturated polyester used in fibers, a film, a bottle and others with ease and a low cost, a solution decomposing saturated polyester and a decomposition method using the solution.

32 Claims, No Drawings

METHOD FOR DISSOLVING SATURATED POLYESTER SOLUTION FOR DECOMPOSING SATURATED POLYESTER AND METHOD FOR DECOMPOSITION USING THE SAME

TECHNICAL FIELD

The present invention relates to a dissolution method for saturated polyester, a solution decomposing saturated polyester and a decomposition method using the solution, and more particularly, to a dissolution method dissolving or decomposing saturated polyester to thereby enable a monomer or a prepolymer of the saturated polyester to be recovered and recycled, a solution decomposing saturated polyester and a decomposition method using the solution.

BACKGROUND ART

Since saturated polyester represented by polyalkylene terephthalate is excellent in characteristics such as strength, transparency, heat resistance and chemical resistance, it has been used in various applications such as fibers, a film, a bottle and others.

In recent years, however, a great problem has been arisen with respect to recycling of spent saturated polyester occurring in an increasing amount or of a disqualified product occurring in production process for saturated polymer, along with an increase in use amount thereof from the viewpoint of the global environment. Recycling methods for saturated polyester currently adopted are classified into three methods in a broad sense, that is a material recycling method, a thermal recycling method and a chemical recycling method.

As the material recycling method, there have been known a method melting saturated polyester to mix it with a virgin raw material to reuse the mixture, a method using only a recovered product to produce a low grade product and the like method. Since a recycled product obtained by means of the material recycling method is low in strength, a necessity arises for a measure to mix a recovered product with a virgin raw material. Since mixing of another plastic into saturated polyester has a problem to greatly reduce strength of a recycled product or color it, a necessity arises for selecting only saturated polyester strictly prior to melting.

While the thermal recycling method reuses heat generated in burning recovered saturated polyester instead of a fuel, saturated polyester is burned in the method; therefore, it is not recycling and a problem arises in an environmental aspect because of generation carbon dioxide in combustion.

The chemical recycling method converts an abandoned saturated polyester product back to a raw material to again synthesize saturated polyester from the raw material, which enables recycling a resource that is an essential object, and which facilitates solving of the problems such as contamination, mixing-in of different resin, reduction in molecular weight in molding, thermal coloration; therefore it is considered to be the best recycling method. Examples of the chemical recycling method include: (1) a hydrolysis method in which saturated polyester is heat-treated together with a strong acid or alkali aqueous solution to thereby convert the saturated polyester to phthalic acid as a dicarboxylic acid such as terephthalic acid or a salt thereof for recovery, (2) a methanol decomposition method in which saturated polyester is heat treated together with methanol to convert it dicarboxylic acid dimethyl ester such as dimethyl terephthalate for recovery and (3) a glycol decomposition method in which saturated polyester is heat treated together with a glycol such as ethylene glycol or propylene glycol and thereby depolymerized to recover prepolymers of saturated polyester. Examples thereof include: a method described in JP-A No. 11-302208 using sodium hydroxide as a catalyst, a method described in JP-A No. 11-322677 in which glycol decomposition is followed by methanol decomposition, a method described in JP-A No. 2000-53802 or 2000-169623 regenerating polyethylene terephthalate, a method described in JP-A No. 2000-191766 using a titanium compound or a tin compound as a catalyst, a method described in JP-A No. 2000-198876 in which plastics other than polyethylene terephthalate are separated off and a method described in JP-A No. 2000-302707 using iron oxide as a catalyst.

In a chemical recycling method for saturated polyester currently available, however, high temperature in the vicinity of 200° C. is necessary in order to advance an ester exchange reaction, which therefore has led to a problem to be unpreferable in regard to energy consumption. In a case where an ester exchange reaction is performed using a low-molecular-weight alcohol, the reaction is often performed under high pressure in order to prevent the alcohol to be evaporated off, having led to problem of a need for an expensive high pressure vessel.

DISCLOSURE OF THE INVENTION

It is an object of the present invention to provide a dissolution method for saturated polyester in which the saturated polyester can be recycled with ease and cost efficiency using a solution that can dissolve saturated polyester even at low temperature under ordinary pressure.

It is another object of the present invention to provide a solution that can selectively disconnect an ester bond of saturated polyester even at low temperature under ordinary pressure to produce a stable compound serving as a raw material of saturated polyester.

It is another object of the present invention to provide a decomposition method for saturated polyester in which the saturated polyester can be recycled with ease and cost efficiency using a solution that can decompose the saturated polyester.

That is, the present invention relates to a dissolution method for saturated polyester in which the saturated polyester is dissolved using an amide solvent.

A dissolution method of the present invention is especially effective in a case where saturated polyester is polyalkylene terephthalate. It is preferable that an amide solvent is a liquid at room temperature and has a boiling point of 180° C. or higher and the amide solvent is especially N-methylpyrrolidone. The dissolution of saturated polyester is preferably performed under ordinary pressure, and a temperature of an amide solvent in dissolution of saturated polyester is preferably a temperature equal to or higher than a freezing point thereof and equal to or lower than a boiling point thereof and especially preferably in the range of from 130 to 190° C.

The present invention relates to a solution for decomposing saturated polyester that contains an alkali and a monoalcohol as a solvent or that contains a salt of a phosphorus-containing acid and a monoalcohol as a solvent.

Saturated polyester decomposed by a solution of the present invention is polyalkylene terephthalate especially with efficiency. A monoalcohol is preferably a lower alcohol and especially preferably methanol.

In a case where a solution of the present invention contains an alkali and a monoalcohol as a solvent as a feature, the solution preferably does not contain a solvent other than a monoalcohol. In a case where a solution of the present invention contains a salt of a phosphorus-containing acid and a monoalcohol as a solvent as a feature, the solution preferably further contains, as a solvent other than a monoalcohol, at least one kind selected from the group consisting of an amide solvent, a ketone solvent, an ether solvent, an ester solvent and a hydrocarbon solvent. A salt of a phosphorus-containing acid is preferably in the form of a hydrate thereof, more preferably an alkali metal salt of a phosphorus-containing acid and especially preferably potassium phosphate.

The present invention relates to a decomposition method for saturated polyester in which the saturated polyester is decomposed using a solution containing an alkali and a monoalcohol or a salt of a phosphorus-containing acid and a monoalcohol.

A decomposition method of the present invention is especially effective in a case where saturated polyester is a polyalkylene terephthalate. The decomposition of the present invention is preferably implemented under ordinary pressure, and a temperature of a solution in the decomposition is preferably equal to or higher than a freezing point thereof and equal to or lower than a boiling point thereof and more preferably equal to or less than 150° C.

At least one kind of decomposition product of saturated polyester obtained by a decomposition method of the present invention is a dicarboxylic acid dialkyl ester or a diol and the decomposition product can be obtained in one step chemical reaction.

The present application claims priority from Japanese patent application Nos. 2001-351068 (filed on Nov. 16, 2001), 2001-351073 (filed on 16 Nov. 2001), 2001-351076 (filed on 16 Nov. 2001), 2001-351081 (filed on 16 Nov. 2001) and 2001-351082 (filed on 16 Nov. 2001), the disclosures of which are incorporated by reference herein.

BEST MODE FOR CARRYING OUT THE INVENTION

Saturated polyester used in a dissolution method, a solution and a decomposition method of the present invention is a polymer obtained by polymerization of a dicarboxylic acid with a diol or a dicarboxylic acid ester with a diol.

Examples of dicarboxylic acids include terephthalic acid, phthalic anhydride, isophthalic acid, adipic acid, naphthalenedicarboxylic acid, chlorendic anhydride, tetrabromophthalic anhydride, tetrahydrophthalic anhydride, tetrachlorophthalic anhydride, succinic acid, glutaric acid, trimellitic anhydride, cyclopentadiene-maleic anhydride adduct and others.

Examples of dicarboxylic acid esters include dialkyl esters of a dicarboxylic acid described above, such as dimethyl ester thereof, diethyl ester thereof, dipropyl ester thereof and dibutyl ester thereof.

Examples of diols include ethylene glycol, 1,4-butanediol, 1,4-cyclohexanedimethanol, propylene glycol, diethylene glycol, neopentyl glycol, dipropylene glycol, dibromoneopentyl glycol, tripropylene glycol, triethylene glycol, polyalkylene glycol, cyclohexanedimethanol, trimethyl pentanediol, dihydroxydicyclopentanediol, bisphenol A, tetrabromobisphenol A, dialkoxybisphenol A, dialkoxytetrabromobisphenol A, hydroquinone, resorcinol, catechol; polycyclic bifunctional phenols such as bisphenol A, bisphenol F, biphenol, dihydroxydiphenyl ether and dihydroxydiphenylsilfone, and halogenides, alkyl group substituted compounds and isomers thereof.

Saturated polyester of the present invention may be obtained by combining several kinds selected from the group consisting of the dicarboxylic acids, the dicarboxylic acid esters and the diols, and may also be obtained by the combination in the presence of a catalyst if necessary. Saturated polyester of the present invention may contain an inorganic filler such as glass fibers, glass powder, calcium carbonate, aluminum hydroxide, magnesium hydroxide, calcium silicate, mica, clay, titania, alumina, iron oxide, aluminum or the like.

Of saturated polyesters having constituents described above, alkylene terephthalate such as polyethylene terephthalate and polybutylene terephthalate are dissoluble or decomposable especially with good efficiency by a dissolution or decomposition reaction of the present invention.

Then, description will be given of a dissolution method for saturated polyester as described above.

In a dissolution method of the present invention, saturated polyester is dissolved in an amide solvent. Examples of amide solvents that can be used in the dissolution include formamide, N-methylformamide, N,N-dimethylformamide, N,N-diethylformamide, acetamide, N-methylacetamide, N,N-dimethylacetamide, N,N,N',N'-tetramethylurea, 2-pyrrolidone, N-methyl-2-pyrrolidone, caprolactam, carbamic acid ester and the like, which are not specifically limited. The amide solvents may be used either alone or in mixture of two or more kinds. Of the amide solvents, preferable with respect to the purpose to efficiently perform a dissolution reaction of the present invention is an amide solvent that is a liquid at room temperature and has a boiling point of 180° C. or higher and especially preferable is N-methylpyrrolidone. A use amount of an amide solvent in the present invention is preferably in the range of from 0.5 to 100 parts by weight and more preferably in the range of from 1 to 10 parts by weight relative to 1 part by weight of saturated polyester.

Any of other solvents may be mixed with saturated polyester and an amide solvent as far as it does not react with the saturated polyester and the amide solvent. Examples of such other solvents include a ketone solvent, an ether solvent, a hydrocarbon solvent, water and others.

Examples of ketone solvents include acetone, methyl ethyl ketone, 2-pentanone, 3-pentanone, 2-hexanone, methyl isobutyl ketone, 2-heptanone, 4-heptanone, diisobutyl ketone, cyclohexanone, methylcyclohexanone, acetophnone, phorone, isophorone and others.

Examples of ether solvents include dipropyl ether, diisopropyl ether, dibutyl ether, dihexyl ether, anisole, phenetole, dioxane, tetrahydrofuran, acetal, ethylene glycol dimethyl ether, ethylene glycol diethyl ether, diethylene glycol dimethyl ether, diethylene glycol diethyl ether and others.

Examples of hydrocarbon solvents include hexane, heptane, octane, nonane, decane, toluene, xylene, ethyl benzene, diethyl benzene, isomers thereof, halogenides thereof, and mixtures thereof.

In a dissolution method of the present invention, the other solvents can also be used either alone or in mixture of a few kinds in arbitrary proportions.

In a case where saturated polyester is dissolved by means of a dissolution method of the present invention, the saturated polyester is preferably crushed into pieces with proper sizes so as to facilitate the saturated polyester to be decomposed. Crushing is implemented using, for example, an impact crusher, a shear crusher, a compression crusher, a stamping mill, a ball mill, a rod mill and the others. While sizes of crushed pieces are not specifically limited, the sizes are preferably in the range of from 0.1 $cm^3$ to 1 $m^3$ in consideration of a scale of an apparatus. If the sizes are less than 0.1 cm$^3$, crushing takes a longer time, while if the sizes larger than 1 m$^3$, a treatment time is longer, any of which cases conspicuously reduces a treatment efficiency.

A dissolution method for crushed saturated polyester pieces with an amide solvent is not specifically limited and exemplified are a method in which the crushed saturated polyester pieces are immersed in an amide solvent, a method in which an amide solvent is sprayed onto the crushed saturated polyester and the like method.

A temperature at which saturated polyester is dissolved using an amide solvent is not specifically limited as far as a solution assumes a liquid state and is arbitrarily determined so as to be equal to or higher than a freezing point of a solution and equal to or lower than a boiling point thereof from the viewpoint of adjustability in desired decomposition speed, treatability and others, wherein the temperature is preferably in the range of from 130 to 190° C. A surrounding atmosphere in the dissolution may be of an inert gas such as air, nitrogen, argon, carbon dioxide or the like, and a pressure thereof may be ordinary pressure or a pressure lower or higher than the ordinary pressure, among which ordinary pressure is preferable in consideration of safety and simplicity and convenience. In order to raise a dissolution speed, it is effective to increase a temperature or to treat under pressure, or in addition to agitate a solvent during immersion or to provide vibration by ultrasonic wave.

In the dissolution, other plastics than saturated polyester may be mixed thereinto, such as polyethylene, polypopylene, polyvinyl chloride, polyamide, acrylic resin, polystyrene, ABS resin, polyurethane, polybutadiene, polyacetal, silicone resin, polymethylmethacrylate, urea resin, phenol resin, epoxy resin, polyimide and the like. The polymers can be separated with ease after the dissolution since they are not compatible with an amide solvent even if being melted by heat in the dissolution.

Metals, alloys thereof and oxides thereof may be mixed, such as aluminum, iron, zinc, tin, nickel, chromium, silicon and the like, and alloys and oxides thereof. Furthermore, inorganic materials may be mixed, such as glass, sand, alumina, porcelain, pottery and the like. Since the metals, metal oxides and inorganic materials are not decomposed in an amide solvent, they can be easily separated after the treatment.

A solvent is removed from a solution dissolving saturated polyester obtained by the dissolution treatment and thereafter, the residual is heated to melt molded for possibility of recycling.

Then, description will be given of a solution decomposing saturated polyester described above and a decomposition method using the same.

A solution for decomposing saturated polyester of the present invention contains an alkali and a monoalcohol or a salt of a phosphorus-containing acid and a monoalcohol as indispensable components.

Examples of alkalis, which are not specifically limited, used in a solution of the present invention include hydroxides, alcoholates and hydrides of alkali metals such as lithium, sodium, potassium, cesium and the like. The compounds may be used either alone or in mixtures of a few kinds. An impurity may be contained without causing a problem.

Examples of salts of phosphorus-containing acids, which are not specifically limited, include salts of phosphoric acid, hypophosphoric acid, phosphorous acid, hypophosphorous acid, pyrophosphoric acid, trimetaphosphoric acid, tetrametaphosphoric acid, pyrophosphorous acid and others with metals or cations of lithium, sodium, potassium, rubidium, cesium, beryllium, magnesium, calcium, strontium, barium, titanium, zirconium, vanadium, chromium, manganese, iron, cobalt, nickel, copper, zinc, aluminum, tin, ammonium and others. A salt described above may be any of a first salt having one metal atom and two hydrogen atoms, a second salt having two metal atoms and one hydrogen atom and a third salt having three metals; may be any of an acidic salt, an alkaline salt and a neutral salt; and may be a hydrate. The compounds may be used either alone or in mixture of a few kinds. The compounds may contain an impurity. Of the salts of phosphorus-containing acids, alkali metal salts thereof are preferably for the purpose to perform a decomposition reaction of the present invention especially with good efficiency, and especially preferable is potassium phosphate. Also preferable are hydrates of salts of phosphorus-containing acids.

Examples of monoalcohols as solvents used in a solution of the present invention include methanol, ethanol, 1-propanol, 2-propanol, 1-butanol, 2-butanol, iso-butanol, tert-butanol, 1-pentanol, 2-pentanol, 3-pentanol, 2-methyl-1-butanol, iso-pentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, cyclohexanol, 1-methylcyclohexanol, 2-methylcyclohexanol, 3-methylcyclohexanol, 4-methylcyclohexanol, ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, triethylene glycol monomethyl ether, triethylene glycol monoethyl ether, benzyl alcohol, tert-butylbenzyl alcohol, methylbenzyl alcohol and chlorobenzyl alcohol, and isomers thereof. The monoalcohols can be used either alone or in mixtures of a few kinds in arbitrary proportions and can also be added with water. Of the monoalcohols, lower alcohols are preferably used for the purpose to perform a decomposition reaction of the present invention especially with good efficiency and methanol is more preferable.

In a case where a solution is of an alkali and a monoalcohol as a solvent of a solution of the present invention, it is preferable not to contain a solvent other than a monoalcohol, while in a case where a solution is of a salt of a phosphorus-containing acid and a monoalcohol as a solvent of a solution of the present invention, it is preferable to contain additionally a solvent other than a monoalcohol, for example an amide solvent, a ketone solvent, an ether solvent, an ester solvent, a hydrocarbon solvent and others.

Examples of amide solvents include formamide, N-methylformamide, N,N-dimethylformamide, N,N-diethylformamide, acetamide, N-methylacetamide, N,N-dimethylacetamide, N,N,N',N'-tetramethylurea, 2-pyrrolidone, N-methyl-2-pyrrolidone, caprolactam, carbamic acid ester and the like.

Examples of ketone solvents include acetone, methyl ethyl ketone, 2-pentanone, 3-pentanone, 2-hexanone, methyl isobutyl ketone, 2-heptanone, 4-heptanone, diisobutyl ketone, cyclohexanone, methyl cyclohexanone, acetophnone, phorone, isophorone and others.

Examples of ether solvents include dipropyl ether, diisopropyl ether, dibutyl ether, dihexyl ether, anisole, phenetole, dioxane, tetrahydrofuran, acetal, ethylene glycol dimethyl ether, ethylene glycol diethyl ether, diethylene glycol dimethyl ether, diethylene glycol diethyl ether and others.

Examples of ester solvents include ethyl formate, propyl formate, butyl formate, isobutyl formate, pentyl formate, methyl acetate, ethylacetate, propylacetate, isopropylacetate, butyl acetate, isobutyl acetate, pentyl acetate, isopentyl acetate, methoxybutyl acetate, methylpentyl acetate, ethylbutyl acetate, ethylhexyl acetate, cyclohexyl acetate, benzyl acetate, methyl propionate, ethyl propionate, butyl propionate, isopentyl propionate, methyl benzoate, ethyl benzoate, propyl benzoate, butyl benzoate, γ-butyrolactone, ethylene glycol monoacetate, diethylene glycol monoacetate, ethylene glycol diacetate, diethylene glycol diacetate and others.

Examples of hydrocarbon solvents include hexane, heptane, octane, nonane, decane, toluene, xylene, ethyl benzene, diethyl benzene, isomers thereof, halogenides thereof, and mixtures thereof.

The solvents other than the monoalcohols can be used either alone or in mixtures of a few kinds in arbitrary proportions.

A mixing ratio in a solution containing an alkali and a monoalcohol of the present invention is such that an alkali can be adjusted at any concentration preferably in the range of from 0.1 to 90 wt % and more preferably in the range of from 1 to 80 wt % relative to a monoalcohol, which is a solvent. A mixing ratio in a solution containing a salt of a phosphorus-containing acid and a monoalcohol of the present invention is such that a salt of a phosphorus-containing acid can be adjusted at any concentration preferably in the range of from 0.1 to 90 wt % and more preferably in the range of from 1 to 80 wt % relative to a monoalcohol, which is a solvent. In a case of a solution containing a salt of a phosphorus-containing acid and a solvent other than a monoalcohol in addition to the monoalcohol, the salt of a phosphorus-containing acid can be adjusted at any concentration in a similar range relative to a total of the monoalcohol and the solvent other than the monoalcohol. In a case of any of the solutions, if a concentration of an alkali or a salt of a phosphorus-containing acid is less than 0.1 wt %, a decomposition speed of saturated polyester is slow, while if exceeding 90 wt %, it is difficult to prepare the solution. It is not always necessary for an alkali or a salt of a phosphorus-containing acid to be dissolved to the full and a solute is in equilibrium even in a saturated solution in which the alkali or the salt of a phosphorus-containing acid is not all dissolved, which situation is effective for making up for diactivation of the alkali or the salt of aphosphorus-containing acid if the deactivation occurs. Furthermore, an additive agent such as a surfactant may be added to a solution of the present invention.

While no specific limitation is imposed on a temperature at which a solution of the present invention is prepared, it is preferably equal to or higher than a melting point and equal to or lower than a boiling temperature. An surrounding atmosphere may be of air, an inert gas under any of ordinary pressure, a pressure lower or higher than the ordinary pressure.

In a case where saturated polyester is decomposed using a solution of the present invention, the saturated polyester is preferably crushed into pieces with proper sizes to enable the saturated polyester, which is an objective, to be decomposed. Crushing is implemented using, for example, an impact crusher, a shear crusher, and a compression crusher, a stamping mill, a ball mill, a rod mill and the others. While sizes of crushed pieces are not specifically limited, the sizes are preferably in the range of from 0.1 cm$^3$ to 1 m$^3$ in consideration of a scale of an apparatus. If the sizes are less than 0.1 cm$^3$, crushing takes a longer time, while if the sizes are larger than 1 cm$^3$, a treatment time is longer, any of which cases conspicuously reduces treatment efficiency.

A decomposition method for crushed saturated polyester pieces with a solution of the present invention is not specifically limited and exemplified are a method in which the crushed saturated polyester pieces are immersed in a solvent of the present invention, a method in which a solution of the present invention is sprayed onto the crushed saturated polyester and the like method.

A temperature at which saturated polyester is decomposed using a solution of the present invention is not specifically limited as far as the solution assumes a liquid state and is arbitrarily determined so as to be equal to or higher than a freezing point of a solution and equal to or lower than a boiling point thereof from the viewpoint of adjustability in desired decomposition speed, treatability and others, wherein the temperature is preferably equal to or lower than 150° C. and more preferably equal to or lower than 100° C. A surrounding atmosphere in the decomposition may be of air, an inert gas such as nitrogen, argon, carbon dioxide or the like, and a pressure thereof may be ordinary pressure or a pressure lower or higher than the ordinary pressure, among which ordinary pressure is preferable in consideration of safety and simplicity and convenience. In order to raise a decomposition speed, it is effective to increase a temperature and to treat under pressure, and in addition to agitate a solvent during immersion and to provide vibration by ultrasonic waves.

In the decomposition, other plastics than saturated polyester may be mixed thereinto, such as polyethylene, polypopylene, polyvinyl chloride, polyamide, acrylic resin, polystyrene, ABS resin, polyurethane, polybutadiene, polyacetal, silicone resin, polymethyl methacrylate, urea resin, phenol resin, epoxy resin, polyimide and the like. The polymers can be separated with ease after the treatment since they are not decomposed in a solution containing an alkali and a monoalcohol or a solution containing a salt of a phosphorus-containing acid and a monoalcohol.

Metals, alloys thereof and oxides thereof may be mixed, such as aluminum, iron, zinc, tin, nickel, chromium, silicon and the like, and alloys and oxides thereof. Furthermore, inorganic materials may be mixed, such as glass, sand, alumina, porcelain, pottery and the like. Since the metals, metal oxides and inorganic materials are not decomposed in a solution containing an alkali and a monoalcohol or a solution containing a salt of a phosphorus-containing acid and a monoalcohol, they can be easily separated after the treatment.

A decomposition product obtained by a decomposition treatment of the present invention contains at least a dicarboxylic acid dialkyl ester or a diol and no limitation is imposed on a product other than the ester or the diol. In a case where a dicarboxylic acid dialkyl ester is added with an acid and thereby is altered to a dicarboxylic acid, and the dicarboxylic acid is precipitated from the solution when water is added in excess thereinto. The dicarboxylic acid is washed with water and dried to thereby obtain a high purity dicarboxylic acid. The dicarboxylic acid can be reused as a raw material for synthesis of saturated polyester.

A solution of the present invention used more than once is subjected to filtration or the like to remove a decomposition product therefrom and supplemented with an amount of shortage of a salt of a phosphorus-containing acid, an alkali, a monoalcohol or the like, thereby enabling the solution to be used repeatedly many times in order to decompose saturated polyester.

In the present invention, a decomposition product as described above can, in such a way, be obtained by a one step chemical reaction.

While detailed description will be given of the present invention based on examples, it should be understood that the present invention is not limited to the examples.

(Dissolution Percentage of Saturated Polyester)

A plate of 0.35 mm thick made of polyethylene terephthalate (manufactured by Tsutsunaka Plastic Industry Co. LTD. with a trade name of Sanroid Pet Ace EPG100) sold on the market as saturated polyester was cut to obtain test pieces each of 10 mm×30 mm in size. Various amide solvents each in amount of 10.0 g were into respective glass test tubes of 20 ml in volume and a temperature of the solvent in the glass test tubes was kept at 60° C. using an oil bath. The test pieces were weighed and thereafter, immersed in the respective solvents, while aluminum caps were placed thereon in order to prevent the solvents from evaporating therefrom. The test pieces were taken out after a predetermined time elapsed, washed with water, dried and again weighed, and then from a change between masses before and after the immersion of each test piece, a mass of dissolved saturated polyester was calculated as a dissolution percentage.

In Table 1, there are shown conditions for and dissolution percentages of Examples 1 to 5 using various kinds of amide solvents and Comparative Examples 1 to 8 using various solvents other than amide solvents.

TABLE 1

| | Solvents | temperatures (° C.) | time (h) | dissolution percentages (%) |
|---|---|---|---|---|
| Example 1 | N,N-dimethyl acetamide | 160 | 4.0 | 14.4 |
| Example 2 | N-methyl-pyrrolidone | 160 | 4.0 | 71.3 |
| Example 3 | N,N-dimethyl formamide | 140 | 4.0 | 5.8 |
| Example 4 | N,N-dimethyl acetamide | 140 | 4.0 | 3.6 |
| Example 5 | N-methyl-pyrrolidone | 140 | 4.0 | 28.1 |
| Comparative Example 1 | isophorone | 160 | 4.0 | −3.2 |
| Comparative Example 2 | acetopheneone | 160 | 4.0 | −0.7 |
| Comparative Example 3 | diethylene glycol monomethyl ether | 160 | 4.0 | 0 |
| Comparative Example 4 | diethylene glycol diacetate | 160 | 4.0 | −0.7 |
| Comparative Example 5 | diethylene glycol monobutyl ether acetate | 160 | 4.0 | −1.3 |
| Comparative Example 6 | benzyl benzoate | 160 | 4.0 | −3.7 |
| Comparative Example 7 | diethylene glycol dethyl ether | 160 | 4.0 | −0.7 |
| Comparative Example 8 | triethylene glycol dimethyl ether | 160 | 4.0 | −0.8 |

Polyethylene terephthalate in blocks was obtained by distilling solutions of Examples 1 to 5 to thereby remove the solvent.

It was found that in cases where amide solvents were used as shown in Examples 1 to 5, polyethylene terephthalate is dissolved with ease. It was found that in contrast to this, in cases where solvents other than amide solvents were used as shown in Comparative Examples 1 to 8, polyethylene terephthalate was not dissolved though being swollen.

(Decomposition Percentages of Saturated Polyester in Cases Where Decomposition Solutions Containing Alkalis and Monoalcohols Were Used)

In Examples 6 to 15, polyethylene terephthalate (manufactured by Tsutsunaka Plastic Industry Co. LTD with a trade name of Sanroid Pet Ace EPG100) sold on the market as saturated polyester was cut to obtain test pieces each of 0.35 mm thick and 10 mm×30 mm in size; in Example 16, polyethylene butylene terephthalate was cut to obtain a test piece of 0.35 mm thick and 10 mm×30 mm in size; and in Example 17, polyethylene naphthalate was cut to obtain a test piece of 0.35 mm thick and 10 mm×30 mm in size. A predetermined amount of each of solutions containing various kinds of alkalis and monoalcohols, which are solvents, was put into a corresponding glass test tube of 20 ml in volume, the solutions in the glass tubes were mildly stirred at room temperature and thereafter, a temperature in the solvent in the glass test tubes was kept at 60° C. using an oil bath. Masses of the test pieces were weighed and thereafter, the test rubes were immersed in the respective solvents, while aluminum caps were placed thereon in order to prevent the solvents from evaporating off therefrom. The test pieces were taken out after 4 hours elapsed, washed with water, dried and masses of the test pieces were again weighed, and then from a change between masses before and after the immersion of each test piece, a mass of decomposed saturated polyester was calculated as a decomposition percentage.

In Table 2, there are shown conditions for and decomposition percentages of Examples 6 to 17 and Comparative Examples 9 to 11. Note that, in Example 14, a procedure similar to that in Example 6 was adopted with the exception that a cooling device was attached to a test tube and the test piece was immersed in the solution at 64° C. under reflux and in Example 15, a procedure similar to that in Example 6 was adopted with the exception that the test piece was immersed while the solution was agitated with a magnetic stirrer.

TABLE 2

| | Alkalis | Solvents | concentrations (eq/1000 g)[note] | concentration (wt %)[note] | temperature (° C.) | time (h) | decomposition percentages |
|---|---|---|---|---|---|---|---|
| Example 6 | LiOH | MeOH | 1.00 | 2.3 | 60 | 4.0 | 12.9 |
| Example 7 | NaOH | MeOH | 1.00 | 3.8 | 60 | 4.0 | 13.3 |
| Example 8 | KOH | MeOH | 1.00 | 5.3 | 60 | 4.0 | 11.1 |
| Example 9 | LiOCH$_3$ | MeOH | 1.00 | 3.7 | 60 | 4.0 | 10.8 |
| Example 10 | NaOCH$_3$ | MeOH | 1.00 | 5.1 | 60 | 4.0 | 9.3 |
| Example 11 | KOCH$_3$ | MeOH | 1.00 | 6.5 | 60 | 4.0 | 9.8 |
| Example 12 | KOCH$_3$ | DGMM | 1.00 | 5.3 | 60 | 4.0 | 6.0 |

TABLE 2-continued

|  | Alkalis | Solvents | concentrations (eq/1000 g)[note] | concentration (wt %)[note] | temperature (° C.) | time (h) | decomposition percentages |
|---|---|---|---|---|---|---|---|
| Example 13 | LiOH | MeOH | 2.00 | 4.6 | 60 | 4.0 | 22.5 |
| Example 14 | LiOH | MeOH | 1.00 | 2.3 | 64 | 4.0 | 15.1 |
| Example 15 | LiOH | MeOH | 1.00 | 2.3 | 60 | 4.0 | 16.8 |
| Example 16 | LiOH | MeOH | 1.00 | 2.3 | 60 | 4.0 | 13.8 |
| Example 17 | LiOH | MeOH | 1.00 | 2.3 | 60 | 4.0 | 10.3 |
| Comparative Example 9 | — | MeOH | — | — | 60 | 4.0 | 0.2 |
| Comparative Example 10 | — | DGMM | — | — | 60 | 4.0 | 0.0 |
| Comparative Example 11 | KOH | water | 1.00 | 6.5 | 60 | 4.0 | 0.3 |

List of chemical formulae and abbreviated symbols
LiOH: lithium hydroxide, NaOH: sodium hydroxide, KOH: potassium hydroxide, MeOH: methanol, $LiOCH_3$: lithium methoxide, $NaOCH_3$: sodium methoxide, $KOCH_3$: potassium methoxide, DGMM: diethylene glycol monomethyl ether
[note]Concentration (eq/1000 g): gram equivalents of a cation/1000 g of a solvent
[note]Concentration (wt %): a concentration of a salt of a phosphorus-containing acid relative to a monoalcohol In Examples 6 to 11, 16 and 17, decomposition percentages were about 10% irrespective of relative low concentrations of various kinds of alkalis. By refluxing a solution with a cooling device mounted to a reaction apparatus as in Example 14 or by treating while being agitated as in Example 15, decomposition percentages can be raised. On the other hand, in Comparative Examples 9 to 11, no decomposition percentage of 1% or higher were not be obtained.

Water in the same amount as the solutions obtained in Examples 6 to 17 was added into the solutions and then a concentrated hydrochloric acid was added into the solutions till the solutions becomes acidic, when white crystals were precipitated. The white crystals were filtered out, washed with water, dried and measured with respect to infrared spectra thereof using Hitachi infrared spectrophotometer, Model No. 270-30 and measured with respect to nuclear magnetic resonance spectra of 1H and 13C using a nuclear magnetic resonance apparatus BRUKER AC300P and, as a result, were identified as terephthalic acid.

(Decomposition Percentages of Saturated Polyester in Cases Where Decomposition Solutions Containing Salts of Phosphorus-containing Acids and Monoalcohols Were Used)

A plate of 0.35 mm thick made of polyethylene terephthalate (manufactured by Tsutsunaka Plastic Industry Co. LTD. with a trade name of Sanroid Pet Ace EPG100) sold on the market as saturated polyester was cut to obtain test pieces of 10 mm×30 mm in size. A predetermined amount of each of solutions containing various kinds of salts of phosphorus-containing acids and monoalcohols, which are solvents, was weighed and put into a corresponding glass test tube of 20 ml in volume, the solutions in the glass tubes were mildly stirred at room temperature. Then, a temperature in the solvent in the glass test tubes was kept at a predetermined temperature using an oil bath. Masses of the test pieces were weighted and thereafter, the test tubes were immersed into the respective solutions and received a treatment, while aluminum caps were placed thereon in order to prevent the solvents from evaporating off therefrom. The test pieces were taken out after predetermined times elapsed, washed with water, dried and again weighed, and then from a change between masses before and after the immersion of each test piece, a proportion of dissolved saturated polyester was calculated as a dissolution percentage.

In Table 3, there are shown conditions for and decomposition percentages of Examples 18 to 65 and Comparative Examples 12 to 16.

TABLE 3

|  | Salts of phosphorus-containing acids | mono-alcohols (solvent 1) | solvent 2 | solvent 1/ solvent 2 (weight ratio) | concentrations (eq/1000 g)[note] | concentrations (wt %)[note] | temperature (° C.) | time (h) | decomposition percentages (%) |
|---|---|---|---|---|---|---|---|---|---|
| Example 18 | $Na_3PO_4$ | MeOH | — | — | 1.00 | 5.2 | 60 | 4.0 | 1.8 |
| Example 19 | $K_2HPO_4$ | MeOH | — | — | 1.00 | 8.0 | 60 | 4.0 | 1.2 |
| Example 20 | $(NH_4)_3PO_4$ | MeOH | — | — | 1.00 | 4.7 | 60 | 4.0 | 2.0 |
| Example 21 | $K_4P_2O_7$ | MeOH | — | — | 1.00 | 7.6 | 60 | 4.0 | 1.4 |
| Example 22 | $K_3PO_4$ | MeOH | — | — | 1.00 | 6.6 | 60 | 4.0 | 12.1 |
| Example 23 | $K_3PO_4$ | EtOH | — | — | 1.00 | 6.6 | 60 | 4.0 | 2.7 |
| Example 24 | $K_3PO_4$ | DGMM | — | — | 1.00 | 6.6 | 60 | 4.0 | 3.0 |
| Example 25 | $K_3PO_4$ | BZA | — | — | 1.00 | 6.6 | 60 | 4.0 | 2.6 |
| Example 26 | $K_3PO_4$ | DGMM | — | — | 1.00 | 6.6 | 160 | 4.0 | 36.4 |
| Example 27 | $K_3PO_4$ | BZA | — | — | 1.00 | 6.6 | 160 | 4.0 | 43.3 |
| Example 28 | $K_3PO_4$ | MeOH | — | — | 2.00 | 12.4 | 60 | 4.0 | 22.6 |
| Example 29 | $K_3PO_4$ | MeOH | — | — | 5.00 | 26.1 | 60 | 4.0 | 42.6 |
| Example 30 | $K_3PO_4$ | MeOH | — | — | 10.00 | 41.4 | 60 | 4.0 | 65.9 |
| Example 31 | $K_3PO_4$ | MeOH | — | — | 20.00 | 58.6 | 60 | 4.0 | 82.9 |
| Example 32 | $K_3PO_4$ | MeOH | — | — | 10.00 | 41.4 | 60 | 2.0 | 33.2 |
| Example 33 | $K_3PO_4$ | MeOH | — | — | 10.00 | 41.4 | 60 | 6.0 | 56.8 |

TABLE 3-continued

| | Salts of phosphorus-containing acids | mono-alcohols (solvent 1) | solvent 2 | solvent 1/ solvent 2 (weight ratio) | concentrations (eq/1000 g)[note] | concentrations (wt %)[note] | temperature (° C.) | time (h) | decomposition percentages (%) |
|---|---|---|---|---|---|---|---|---|---|
| Example 34 | $K_3PO_4$ | MeOH | — | — | 10.00 | 41.4 | 60 | 10.0 | 86.7 |
| Example 35 | $K_3PO_4$ | MeOH | — | — | 20.00 | 58.6 | 60 | 2.0 | 47.9 |
| Example 36 | $K_3PO_4$ | MeOH | — | — | 20.00 | 58.6 | 60 | 6.0 | 72.2 |
| Example 37 | $K_3PO_4$ | MeOH | — | — | 20.00 | 58.6 | 60 | 10.0 | 100.0 |
| Example 38 | $Na_3PO_4.12H_2O$ | MeOH | — | — | 1.00 | 11.2 | 60 | 4.0 | 2.2 |
| Example 39 | $K_3PO_4.nH_2O$ | MeOH | — | — | 1.00 | 8.3 | 60 | 4.0 | 6.1 |
| Example 40 | $K_3PO_4.nH_2O$ | EtOH | — | — | 1.00 | 8.3 | 60 | 4.0 | 2.9 |
| Example 41 | $K_3PO_4.nH_2O$ | DGMM | — | — | 1.00 | 8.3 | 60 | 4.0 | 2.8 |
| Example 42 | $K_3PO_4.nH_2O$ | BZA | — | — | 1.00 | 8.3 | 60 | 4.0 | 3.2 |
| Example 43 | $K_3PO_4.nH_2O$ | DGMM | — | — | 1.00 | 8.3 | 160 | 4.0 | 38.5 |
| Example 44 | $K_3PO_4.nH_2O$ | BZA | — | — | 1.00 | 8.3 | 160 | 4.0 | 41.4 |
| Example 45 | $K_3PO_4.nH_2O$ | MeOH | — | — | 2.00 | 15.3 | 60 | 4.0 | 7.0 |
| Example 46 | $K_3PO_4.nH_2O$ | MeOH | — | — | 5.00 | 31.2 | 60 | 4.0 | 14.1 |
| Example 47 | $K_3PO_4.nH_2O$ | MeOH | — | — | 10.00 | 47.6 | 60 | 4.0 | 18.1 |
| Example 48 | $K_3PO_4.nH_2O$ | MeOH | — | — | 20.00 | 64.5 | 60 | 4.0 | 27.4 |
| Example 49 | $K_3PO_4.nH_2O$ | MeOH | — | — | 1.00 | 47.6 | 60 | 10.0 | 32.1 |
| Example 50 | $K_3PO_4.nH_2O$ | MeOH | — | — | 10.00 | 47.6 | 60 | 10.0 | 73.2 |
| Example 51 | $K_3PO_4.nH_2O$ | MeOH | — | — | 20.00 | 47.6 | 60 | 10.0 | 54.7 |
| Example 52 | $K_3PO_4.nH_2O$ | MeOH | — | — | 1.00 | 64.5 | 60 | 20.0 | 55.4 |
| Example 53 | $K_3PO_4.nH_2O$ | MeOH | — | — | 10.00 | 64.5 | 60 | 20.0 | 91.1 |
| Example 54 | $K_3PO_4.nH_2O$ | MeOH | — | — | 20.00 | 64.5 | 60 | 20.0 | 100.0 |
| Example 55 | $K_3PO_4$ | MeOH | water | 1.0/1.0 | 1.00 | 8.3 | 60 | 4.0 | 2.7 |
| Example 56 | $K_3PO_4$ | MeOH | acetophenone | 1.0/1.0 | 1.00 | 6.6 | 60 | 4.0 | 24.0 |
| Example 57 | $K_3PO_4$ | MeOH | methyl ethyl ketone | 1.0/1.0 | 1.00 | 6.6 | 60 | 4.0 | 28.3 |
| Example 58 | $K_3PO_4$ | MeOH | acetone | 1.0/1.0 | 1.00 | 6.6 | 60 | 4.0 | 23.2 |
| Example 59 | $K_3PO_4$ | MeOH | N,N-dimethyl formamide | 1.0/1.0 | 1.00 | 6.6 | 60 | 4.0 | 22.7 |
| Example 60 | $K_3PO_4$ | MeOH | N,N-dimethyl acetamide | 1.0/1.0 | 1.00 | 6.6 | 60 | 4.0 | 27.6 |
| Example 61 | $K_3PO_4$ | MeOH | N-methyl pyrrolidone | 1.0/1.0 | 1.00 | 6.6 | 60 | 4.0 | 28.4 |
| Example 62 | $K_3PO_4$ | MeOH | ethylene glycol diacetate | 1.0/1.0 | 1.00 | 6.6 | 60 | 4.0 | 29.4 |
| Example 63 | $K_3PO_4$ | MeOH | toluene | 1.0/1.0 | 1.00 | 6.6 | 60 | 4.0 | 28.7 |
| Example 64 | $K_3PO_4.nH_2O$ | MeOH | N,N-dimethyl acetamide | 1.0/1.0 | 1.00 | 8.3 | 60 | 4.0 | 27.6 |
| Example 65 | $K_3PO_4$ | MeOH | N,N-dimethyl acetamide. | 1.0/1.0 | 10.00 | 41.4 | 60 | 4.0 | 77.2 |
| Comparative Example 12 | — | MeOH | — | — | — | — | 60 | 4.0 | 0.2 |
| Comparative Example 13 | — | EtOH | — | — | — | — | 60 | 4.0 | 0.3 |
| Comparative Example 14 | — | DGMM | — | — | — | — | 160 | 4.0 | 0.1 |
| Comparative Example 15 | — | BZA | — | — | — | — | 160 | 4.0 | 0.2 |
| Comparative Example 16 | $K_3PO_4$ | — | acetophenone | — | — | — | 160 | 4.0 | −0.7 |

List of chemical formulae and abbreviated symbols
$Na_3PO_3$: trisodium phosphate, $Na_3PO_4.12H_2O$: trisodium phosphate dodecahydrate, $K_3PO_4.nH_2O$:tripotassium phosphate n-hydrate (a trade name, manufactured by KANTO KAGAKU with a content of tripotassium phosphate in the range of 74 to 85%),$K_2HPO_4$: dipotassium phosphate, $(NH_4)_3PO_4$: triammonium phosphate, $K_4P_2O_7$: potassium pyrophosphate,$K_3PO_4$: tripotassium phosphate, MeOH: methanol,
[note]Concentration (eq/1000 g): gram equivalents of a cation/1000 g of a solvent
[note]Concentration (wt %): a concentration of a salt of a phosphorus-containing acid relative to a monoalcohol As shown in Table 3, in Examples 18 to 65 using solutions containing various kinds of salts of a phosphorus-containing acids and monoalcohols, decomposition percentages were all shown to be 1% or more. Among them, as shown in Example 37, conditions were found that polyethylene terephthalate is all decomposed at 60° C. for 10 h. In cases where solvents other than methanol were used together with methanol as shown in Examples 56 to 65, decomposition percentages were shown to be all larger than in a case where methanol alone was used by a factor in the range of from about 2 to 4. In contrast to the examples, in Comparative Examples 12 to 15, decomposition percentages were all 1% or less since the treatments were performed with solutions containing monoalcohols only without containing salts of a phosphorus-containing acids and in Comparative Example 16, a decomposition percentage was 1% or less since a monoalcohol was not used as a solvent.

In Examples 18 to 37 and 46 to 54, water in amount ten times as much as that of each solution was added to the solution after the corresponding decomposition treatment, while in Examples 56 to 65, water in amount ten times as much as that of each solution was added to the solution after the corresponding treatment, whereby white crystals were precipitated. Then, the solvents were removed by filtration, the salts of phosphorus-containing acids were removed by washing the crystals with water and thereafter, the crystals were dried to obtain white powder. The white powder was measured with respect to infrared spectra thereof using Hitachi infrared spectrophotometer, Model No. 270-30 and measured with respect to nuclear magnetic resonance spectra of 1H and 13C using a nuclear magnetic resonance apparatus BRUKER AC300P and as a result, was identified as dimethyl terephthalate because of coincidence with the spectra of dimethyl terephthalate. A purity thereof was 99%.

In each of Examples 18 to 37, a filtrate from the filtration was distilled at 100° C. or lower to remove the solvent and the residual was subjected to filtration to separate a transparent liquid from the salt of a phosphorus-containing salt. As described above, the liquid was measured with respect to infrared spectra thereof and measured with respect to nuclear magnetic resonance spectra of 1H and 13C and as a result, was identified as ethylene glycol because of coincidence with the spectra of ethylene glycol.

In each of Examples 46 to 54, water in amount equal to a filtrate was added to the filtrate and a concentrated hydrochloric acid was added to the diluted filtrate till being acidic, thereby precipitating white crystals. The diluted filtrate was filtered out to isolate the white crystals and the white crystals were washed with water, dried and measured with respect to infrared spectra thereof and nuclear magnetic resonance spectra thereof, and as a result, were identified as terephthalic acid. A purity thereof was 98%. Note that a similar procedure was applied to the filtrate of Example 22, in which case no production of terephthalic acid was observed.

In such a way, polyethylene terephthalate was able to be decomposed into dimethyl terephthalate and ethylene glycol, which are raw materials of polyethylene terephthalate, in one step reaction at a boiling point or lower of a solution under ordinary pressure. Furthermore, in an example using a hydrate of a salt of a phosphorus-containing acid, terephthalic acid was able to be obtained.

Note that in all of the examples, use of a stirrer, a pressure vessel, a cooling device and others promotes an efficiency of dispersion to definitely reduce a treatment time. A treatment at a boiling point of a solvent or higher in a pressure vessel decreases a treatment time. Use of a cooling device enables a long time treatment at the boiling point of a solution to be realized, which definitely reduce a treatment time as well.

According to the present invention, since, as described above, saturated polyester can be dissolved or decomposed under ordinary pressure at a low temperature, saturated polyester can be recycled with more of ease at a lower cost as compared with those in a conventional technique.

A person skilled in the art shall understand that the above description is preferred embodiments of the present invention and many of alterations or modifications thereof can be implemented without departing from the spirit and scope of the present invention.

The invention claimed is:

1. A solution for decomposing saturated polyester containing an alkali and a monoalcohol as a solvent, and not containing a solvent other than the monoalcohol.

2. The solution according to claim 1, wherein the saturated polyester is polyalkylene terephthalate.

3. The solution according to claim 1, wherein the monoalcohol is a lower alcohol.

4. The solution according to 1, wherein the monoalcohol is methanol.

5. A solution for decomposing saturated polyester containing a salt of a phosphorus-containing acid and a monoalcohol as a solvent.

6. The solution according to claim 5, wherein the saturated polyester is polyalkylene terephthalate.

7. The solution according to claim 5, wherein the salt of a phosphorus-containing acid is in the form of a hydrate thereof.

8. The solution according to claim 5, wherein the salt of a phosphorus-containing acid is an alkali metal salt of a phosphorus-containing acid.

9. The solution according to claim 5, wherein the salt of a phosphorus-containing acid is potassium phosphate or potassium phosphate hydrate.

10. The solution according to claim 5, wherein the monoalcohol is a lower alcohol.

11. The solution according to claim 5, wherein the monoalcohol is methanol.

12. The solution according to claim 5, further containing, as a solvent other than a monoalcohol, at least one kind selected from the group consisting of an amide solvent, a ketone solvent, an ether solvent, an ester solvent and a hydrocarbon solvent.

13. A decomposition method for saturated polyester, comprising decomposing the saturated polyester in the presence of the solution according to claim 5.

14. The decomposition method for saturated polyester according to claim 13, wherein the saturated polyester is a polyalkylene terephthalate.

15. The decomposition method for saturated polyester according to claim 13, wherein a temperature of the solution in the decomposition is equal to or higher than a freezing point thereof and equal to or lower than a boiling point thereof.

16. The decomposition method for saturated polyester according to claim 13, wherein a temperature of the solution in the decomposition is equal to or less than 150° C.

17. The decomposition method for saturated polyester according to claim 13, wherein the decomposition is implemented under ordinary pressure.

18. The decomposition method for saturated polyester according to claim 13, wherein at least one kind of decomposition product of the saturated polyester is a dicarboxylic acid dialkyl ester.

19. The decomposition method for saturated polyester according to claim 13, wherein at least one kind of decomposition product of the saturated polyester is a diol.

20. The decomposition method for saturated polyester according to claim 13, wherein the decomposition product of the saturated polyester is obtained in one step chemical reaction.

21. A decomposition method for saturated polyester, comprising decomposing the saturated polyester in the presence of the solution according to claim 1.

22. The decomposition method for saturated polyester according to claim 21, wherein the saturated polyester is a polyalkylene terephthalate.

23. The decomposition method for saturated polyester according to claim 21, wherein a temperature of the solution in the decomposition is equal to or higher than a freezing point thereof and equal to or lower than a boiling point thereof.

24. The decomposition method for saturated polyester according to claim 21, wherein a temperature of the solution in the decomposition is equal to or less than 150° C.

25. The decomposition method for saturated polyester according to claim 21, wherein the decomposition is implemented under ordinary pressure.

26. The decomposition method for saturated polyester according to claim 21, wherein at least one kind of decomposition product of the saturated polyester is a dicarboxylic acid dialkyl ester.

27. The decomposition method for saturated polyester according to claim 21, wherein at least one kind of decomposition product of the saturated polyester is a diol.

28. The decomposition method for saturated polyester according to claim 21, wherein the decomposition product of the saturated polyester is obtained in one step chemical reaction.

29. The solution according to claim 1, said solution further comprising said saturated polyester.

30. The solution according to claim 29, wherein said saturated polyester is polyalkylene terephthalate.

31. The solution according to claim 5, said solution further comprising said saturated polyester.

32. The solution according to claim 31, wherein said saturated polyester is polyalkylene terephthalate.

\* \* \* \* \*